(12) United States Patent
Henriksen

(10) Patent No.: US 9,819,864 B2
(45) Date of Patent: Nov. 14, 2017

(54) WIDE FIELD RETINAL IMAGE CAPTURE SYSTEM AND METHOD

(71) Applicant: RSBV, LLC, Fort Collins, CO (US)

(72) Inventor: David Henriksen, Fort Collins, CO (US)

(73) Assignee: RSVB, LLC, Ft. Collins, CO (US)

( * ) Notice: Subject to any disclaimer, the term of this patent is extended or adjusted under 35 U.S.C. 154(b) by 0 days.

(21) Appl. No.: 15/038,319

(22) PCT Filed: Dec. 23, 2014

(86) PCT No.: PCT/US2014/072077
§ 371 (c)(1),
(2) Date: May 20, 2016

(87) PCT Pub. No.: WO2015/100294
PCT Pub. Date: Jul. 2, 2015

(65) Prior Publication Data
US 2016/0295109 A1 Oct. 6, 2016

Related U.S. Application Data

(60) Provisional application No. 61/919,941, filed on Dec. 23, 2013.

(51) Int. Cl.
*H04N 5/232* (2006.01)
*A61B 3/12* (2006.01)
(Continued)

(52) U.S. Cl.
CPC ....... *H04N 5/23238* (2013.01); *A61B 3/0025* (2013.01); *A61B 3/12* (2013.01);
(Continued)

(58) Field of Classification Search
None
See application file for complete search history.

(56) References Cited

U.S. PATENT DOCUMENTS 5,649,032 A 7/1997 Burt
7,377,643 B1* 5/2008 Chock ............... A61B 3/14
351/205
(Continued)

FOREIGN PATENT DOCUMENTS

WO WO 01/28405 A2 4/2001

OTHER PUBLICATIONS

International Search Report and Written Opinion dated Apr. 28, 2015 for corresponding International Patent Application No. PCT/US2014/072077.
(Continued)

*Primary Examiner* — Andy Rao
*Assistant Examiner* — Samuel D Fereja
(74) *Attorney, Agent, or Firm* — Swanson & Bratschun, L.L.C.

(57) ABSTRACT

A method, system or apparatus for generating a wide field retinal image. System embodiments comprise a camera, which may be a smartphone camera and associated optics to capturing a digital video stream of individual retinal images and store the video stream of individual retinal images in a memory associated with the camera. The system or method then implements the steps of processing each retinal image and combining selected retinal images into a panorama in real time, during an ocular examination.

18 Claims, 9 Drawing Sheets

(51) Int. Cl.
  *A61B 3/00*    (2006.01)
  *A61B 3/14*    (2006.01)
  *G06K 9/62*    (2006.01)
  *G06T 3/40*    (2006.01)
  *G06T 7/33*    (2017.01)
  *G06T 7/13*    (2017.01)
  *G06T 7/136*   (2017.01)

(52) U.S. Cl.
  CPC .............. *A61B 3/14* (2013.01); *G06K 9/6202*
    (2013.01); *G06T 3/4038* (2013.01); *G06T 7/13*
    (2017.01); *G06T 7/136* (2017.01); *G06T 7/33*
    (2017.01); *G06T 2207/20164* (2013.01); *G06T*
    *2207/20221* (2013.01); *G06T 2207/30041*
    (2013.01)

(56) References Cited

U.S. PATENT DOCUMENTS

| | | | |
|---|---|---|---|
| 2007/0252951 A1* | 11/2007 | Hammer | A61F 9/008 351/221 |
| 2010/0194851 A1 | 8/2010 | Pasupaleti | |
| 2010/0289922 A1 | 11/2010 | Brenner et al. | |
| 2011/0242306 A1* | 10/2011 | Bressler | A61B 3/12 348/78 |
| 2012/0130270 A1* | 5/2012 | Imamura | G06T 7/0012 600/558 |
| 2012/0184845 A1* | 7/2012 | Ishikawa | A61B 3/102 600/425 |
| 2013/0033593 A1* | 2/2013 | Chinnock | A61B 3/0091 348/78 |
| 2013/0033677 A1* | 2/2013 | MacDougall | A61B 3/113 351/206 |
| 2013/0083185 A1 | 4/2013 | Coleman | |
| 2013/0293671 A1 | 11/2013 | Gorstan | |
| 2013/0329190 A1* | 12/2013 | Lewis | G02B 27/017 351/246 |
| 2014/0160264 A1* | 6/2014 | Taylor | G02B 21/008 348/79 |
| 2014/0228668 A1* | 8/2014 | Wakizaka | A61B 3/14 600/407 |
| 2015/0029322 A1* | 1/2015 | Ragland | G06K 9/00604 348/78 |
| 2015/0110372 A1* | 4/2015 | Solanki | G06T 7/0014 382/130 |
| 2016/0166141 A1* | 6/2016 | Kanagasingam | G06T 7/0012 351/206 |

OTHER PUBLICATIONS

Extended European Search Report, dated Aug. 8, 2017, 9 pages.
Becker et al., 1998, IEEE Transactions on Biomedical Engineering, vol. 45 No. 1, 14 pages.

* cited by examiner

| Image Frames 1&2 | Marked Point Positions |
|---|---|
|  | PT#1 (448, 127)<br>PT#2 (508, 94)<br>PT#3 (512, 119)<br>PT#4 (499, 129) |
|  | ...<br>PT#10 (137, 519)<br>PT#11 (195, 490)<br>PT#12 (198, 512)<br>PT#13 (183, 522) |

Fig. 9

WIDE FIELD RETINAL IMAGE CAPTURE SYSTEM AND METHOD

RELATED APPLICATIONS

This application is a 35 U.S.C. §371 national phase application of PCT/US14/072077 (WO 2015/100294), filed on Dec. 23, 2014, entitled "Wide Field Retinal Image Capture System and Method", which application claims the benefit of U.S. Provisional Application Ser. No. 61/919,941, filed Dec. 23, 2013, which is incorporated herein by reference in its entirety.

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to methods, systems, apparatus, and computer software for capturing wide field retinal images.

BACKGROUND

Capturing wide-field retinal images is traditionally a very challenging process. Because of the basic anatomy of the human eye, imaging the retina requires illumination of the retina with an external light source projecting illumination through the patient's pupil while simultaneously capturing a retinal image through the same pupil while avoiding or minimizing glare from the light source.

Pupil dilation techniques are able to create a much larger pupil opening for examination purposes. Even so, very precise alignment is needed for retinal imaging even with pupil dilation. The distance that the imaging system is positioned from the front of the cornea is particularly critical, as being either too far away or too close will result in corneal glare from the light source. Therefore, stationary tabletop retinal imaging systems are generally much easier to operate than handheld retinal cameras because of the precise alignment and enhanced stability provided by a tabletop system.

Tabletop retinal imaging systems are, expensive and difficult to move. Therefore tabletop systems are not well-suited to use in the field, in remote clinics, or in multipurpose examination clinics lacking dedicated ophthalmological equipment. Accordingly, various companies and educational institutions have started to develop and conduct clinical trials utilizing simple and inexpensive smartphone attachments that allow for the capture of retinal images. These attachments range from simple brackets that hold an ophthalmic lens in front of a smartphone to small devices that place a light source suitable for illuminating the retina very close to the smartphones camera lens to allow retinal images to be captured using the camera's existing optics.

Unlike traditional retinal imaging systems, the retinal images that are captured with smartphone attachments of this nature can appear anywhere on the smartphone image sensor, and the position of the useable portion of the retinal image can continuously move around on the image sensor during the retinal exam since a smartphone-based imaging system is typically handheld. In addition, the field of view of retinal imaging systems greatly influences the ease of use of these systems. In particular, camera systems that have a narrower field of view inherently require less precision in terms of alignment position and working distance than wider field of view camera systems. Because of this, handheld camera systems, including smartphone-based systems, generally have a considerably narrower field of view than stationary tabletop systems that provide a chin rest to keep the patient's head from moving during the exam. Unfortunately, retinal screening for medical conditions requires a much wider field of view than typical hand-held camera or smartphone-based system can readily provide.

The use of panorama image preparation can in certain instances remedy and inherently narrow field of view. Traditional retinal image panorama construction requires the camera operator to capture multiple still shots of various regions of the eye, and to run a post-image acquisition process in which the operator manually selects images that are believed can be suitably stitched together by software designed to construct the image panorama. Thus panorama preparation is typically performed after the patient exam. This process has several problems, the main one of which is that the camera operator may find out that the images that they have captured are not adequate for construction of the panorama until after the patient's exam has been completed and they are already working with the next patient.

The embodiments disclosed herein are directed toward overcoming one or more of the problems noted above.

BRIEF SUMMARY

Various embodiments provide apparatus, systems and techniques for capturing, processing, generating and utilizing wide field images of an ocular structure, in particular of a retina.

Certain embodiments include a method, system or apparatus for generating a wide field retinal image. System embodiments comprise a camera, which may be a smartphone camera and associated optics to capturing a digital video stream of individual retinal images and store the video stream of individual retinal images in a memory associated with the camera. The system or method then implements the steps of processing each retinal image and combining selected retinal images into a panorama in real time, during an ocular examination.

Embodiments include a method, system or apparatus for generating a wide field retinal image comprising a camera, which may be a smartphone camera and associated optics to capturing a digital video stream of individual retinal images and store the video stream of individual retinal images in a memory associated with the camera. The system or method may then include or implement the steps of downsizing an individual retinal image, performing edge detection on the downsized image to yield a binary image and identifying points of interest in the binary image. In addition, the system or method may include the steps of determining the relative position of points of interest in the binary image, populating a data structure with relative positions of points of interest determined from multiple downsized individual retinal images, and comparing the relative point of interest position information among multiple downsized individual retinal images to determine an overlapping image alignment among the plurality of downsized individual retinal images. Full resolution retinal images corresponding to the selected downsized individual retinal images may then be combined into a panorama in accordance with the determined overlapping image alignment.

In certain embodiments, the system or method may further perform the steps of determining a location on a sensor of the camera where an individual image is located, determining a region of interest in the individual image and cropping the individual image to preserve the region of interest. In addition, the system or method may measure one or more image attributes of the downsized images; and discard unsuitable images based upon the measured image attributes of the downsized images. In some embodiments the system or method may determine whether a downsized retinal image is of a higher quality than another downsized retinal image showing an overlapping retinal structure and discard lower quality image.

Prior to termination of a video capture the system or method may measure the field of view of the combined full resolution retinal image and terminating the process upon achievement of a designated field of view.

The embodiments disclosed herein describe methods in which multiple sub images extracted from a continuous series of individual frames from a video stream can be analyzed in real-time at a very high frame-rate to construct an image panorama that completes autonomously after a pre-defined field of view has been achieved for the image panorama. Additionally, when an image frame has been determined to be of better quality than a previously captured image frame from the same region of the eye, the new image frame is retained in the panorama and the original frame is discarded.

One apparatus suitable for the implementation of the described methods includes a smartphone having camera optics and electronics coupled to an existing low cost handheld ophthalmoscope. A smartphone based method is inexpensive, portable and fully functional. The disclosed methods however may also greatly enhance the overall ease of use of a wide range of dedicated or specialized retinal imaging systems from low cost handhelds to high-cost tabletop units.

The disclosed system and methods utilize several algorithm simplification techniques. Thus, the described system and methods allow for real-time processing with very low computational requirements and are therefore suitable for deployment via a smartphone.

Various modifications and additions can be made to the embodiments discussed without departing from the scope of the invention. For example, while the embodiments described above refer to particular features, the scope of this invention also included embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components. In some instances, a sub-label is associated with a reference numeral to denote one of multiple similar components. When reference is made to a reference numeral without specification to an existing sub-label, it is intended to refer to all such multiple similar components.

FIG. 9 is an image comparison of two image frames (represented for convenience as full resolution images) showing overlapping points of interest.

DETAILED DESCRIPTION OF CERTAIN EMBODIMENTS

While various aspects and features of certain embodiments have been summarized above, the following detailed description illustrates a few exemplary embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

Figure 2:
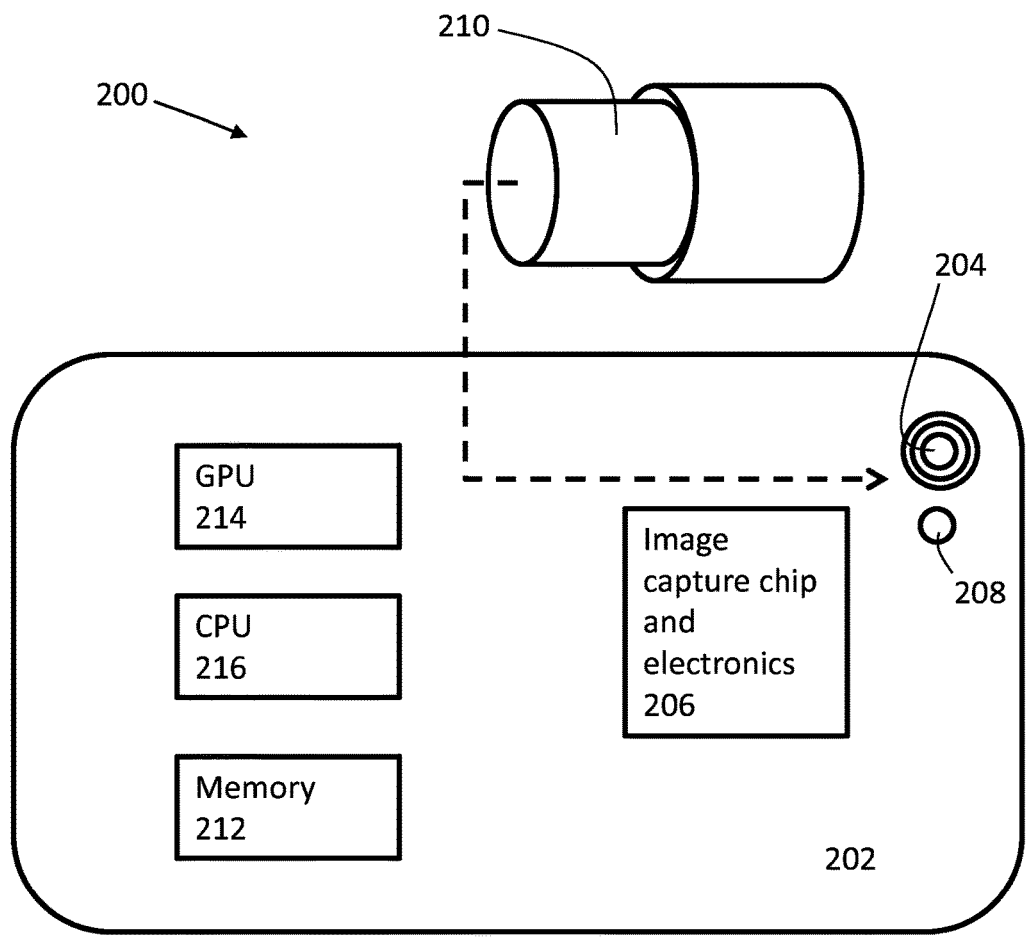
FIG. 2 is a block diagram depiction of a disclosed system embodiment.

One embodiment is an image acquisition and processing method 100 implemented with selected apparatus embodiments disclosed herein. A representative apparatus embodiment is schematically illustrated in FIG. 2. The method and apparatus may be used to capture and process compound or mosaic retinal images having a wider field of view than can be directly provided by the imaging optics and electronics in a single image frame. Wide field retinal images are required in certain examination or diagnostic situations. For example, certain diseases such as diabetic retinopathy may, in certain instances, be detected at the earliest stages by examination of the perimeter of the subject retina, which is a region outside of the field of view of conventional retinal imaging systems. The disclosed systems and methods may be used with human or animal patients. The resulting images may be used to diagnose disease, verify retinal health, prepare a dated record of retinal health status for future comparison with follow-up images and other purposes, or for biometric identification via a subject's vascular retinal pattern.

Certain apparatus or system embodiments, such as illustrated in FIG. 2 may include a smartphone having built-in camera and lighting functionality. Thus the system 200 may include a smartphone 202, a smartphone camera lens 204, an image capture chip and associated electronics 206 and an illumination source 208. The system also includes supplemental optics 210 which may be attached directly to the smartphone 202 in the region of the smartphone camera lens 204 and illumination source 208. Certain other elements of the system are described in detail below.

Although the disclosed methods are well-suited for implementation with a smartphone-based system 200, the image capture and processing techniques are equally well suited to use with dedicated ophthalmoscope systems, dedicated ophthalmoscope cameras or other dedicated or semi-dedicated retinal imaging systems.

Figure 1:
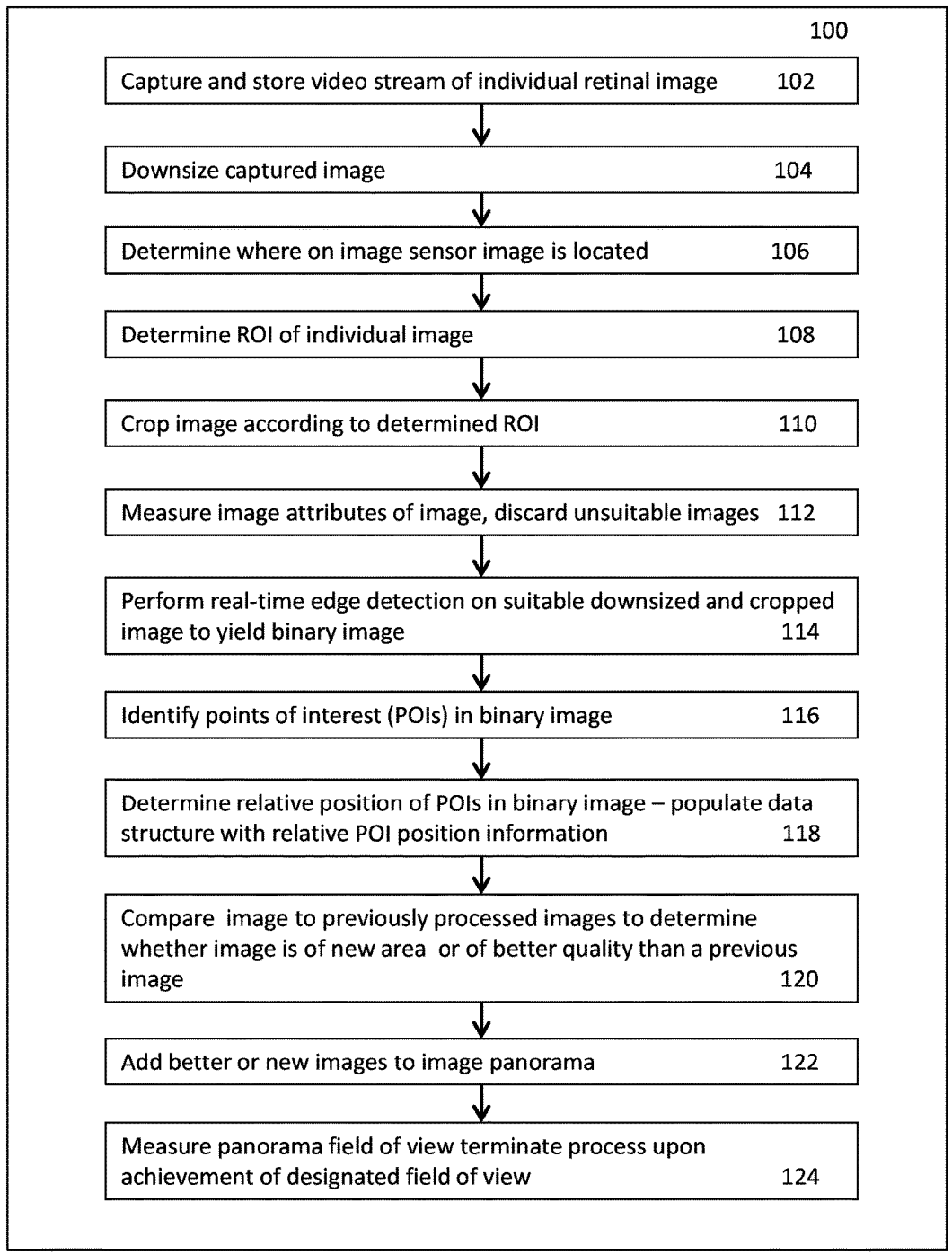
FIG. 1 is a general schematic flow diagram depiction of a method as disclosed herein

One embodiment disclosed herein is a method of capturing and processing the component images required to create a suitable wide-field retinal mosaic. The method 100 illustrated in FIG. 1 may be implemented using the image capture electronics 206 of a smartphone 202 in conjunction with a supplemental lens 210 providing for proper focusing of the smartphone camera optics 204 on the subject retina. Images are captured as a series of video frames. Accordingly, the terms image and frame are used interchangeably herein to define the individual sub-images which comprise a video stream. The initial step in the capture of a wide field retinal image is the capture of a reasonably well focused video stream of the subject retina with a system as described herein (Step 102). The retinal video stream may consist of any number of images or frames which may be stored in the system memory 212 or in certain instances the images are frames of the video stream may be stored in outboard memory.

The operator of the system rotates or pivots the camera and optics, which can in certain instances be a smartphone 202 and supplemental lens 210, with respect to the subject retina while the video stream is being captured, stored and processed as described below. Thus the entire viewable portion of the subject retina, to the extent possible given anatomical and optical constraints, is made the subject of at least one or more frames within the captured video stream. The capture of a video stream, showing as much of the subject retina as physically and optically possible proceeds until system memory is filled or more likely until the process automatically terminates as described below. In certain embodiments, individual frames are analyzed and processed in real time from the camera video stream during the examination. It is not important that the operator capture video of various regions of the retinal surface in any particular order. As described in detail below, the system and method are optimized to prepare a wide field mosaic from sub images or frames captured in any order.

As the video stream is being captured, in real time, one embodiment of the system and method downsize each captured image frame so that the system and method can perform further image processing steps on a lower resolution image to greatly enhance the computation efficiency of the entire process (Step 104). Although the image processing steps are performed on the downsized image, the original higher resolution image data are maintained in memory so that no resolution is lost during other steps, including but not limited to construction of the image panorama. The particular algorithm utilized for the downsizing step is not critical because the system and method is not downsizing the image frame for viewing purposes, but simply to perform edge detection and further processing steps on the image frame as described below. Simple 4×4 pixel averaging performs very well for the described purposes, and this step is ideally performed on the GPU (Graphics processor) 214 of the smartphone, in a smartphone-based system, because the GPU 214 is a substantially processor than the CPU 216 of most smartphones.

Figure 3:
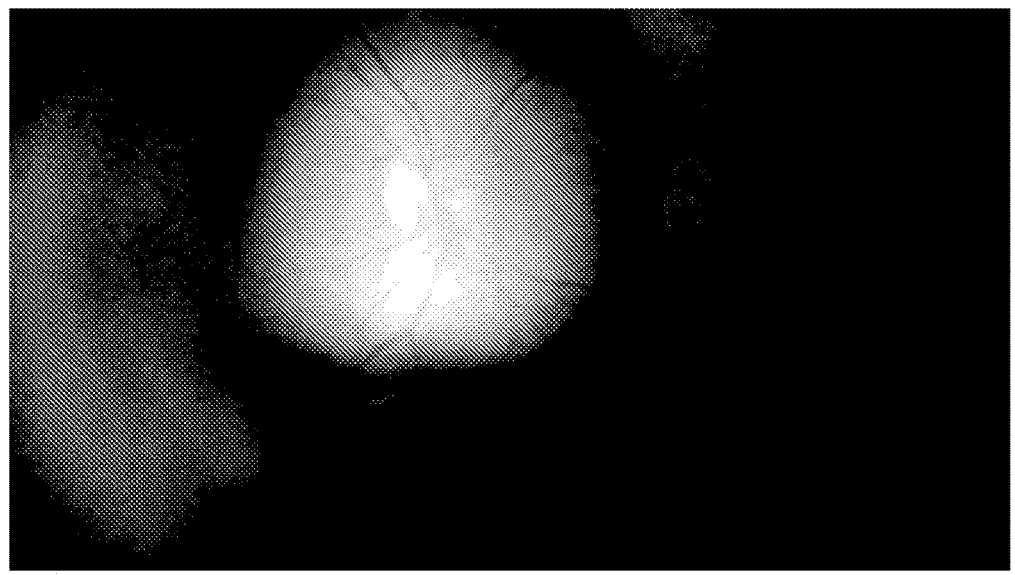
FIG. 3 is an uncropped full frame image containing a region of interest (ROI) and ancillary data.

In selected embodiments, the next image processing step is to determine where on the image sensor the relatively narrow field retinal image is located (Step 106). For example, FIG. 3 is a representative un-cropped full-sensor image. The useful retinal image data of FIG. 3 covers significantly less than the entire image frame. As described below, the determination of the location of the retinal image on the image sensor facilitates the determination of a region of interest (ROI) which can be used to automatically crop out only the useful portion of each image (Steps 108-110). The first step in the process of determining the ROI is to perform an adaptive threshold on the raw image obtained in step 102 which creates a binary image from the original source image. See, for example, the binary full-frame image of FIG. 4. Adaptive thresholding techniques are ideal for image thresholding when different lighting levels may exist for each portion of the image because they adaptive thresholding techniques utilize a different threshold value for each small area of the image.

Figure 4:
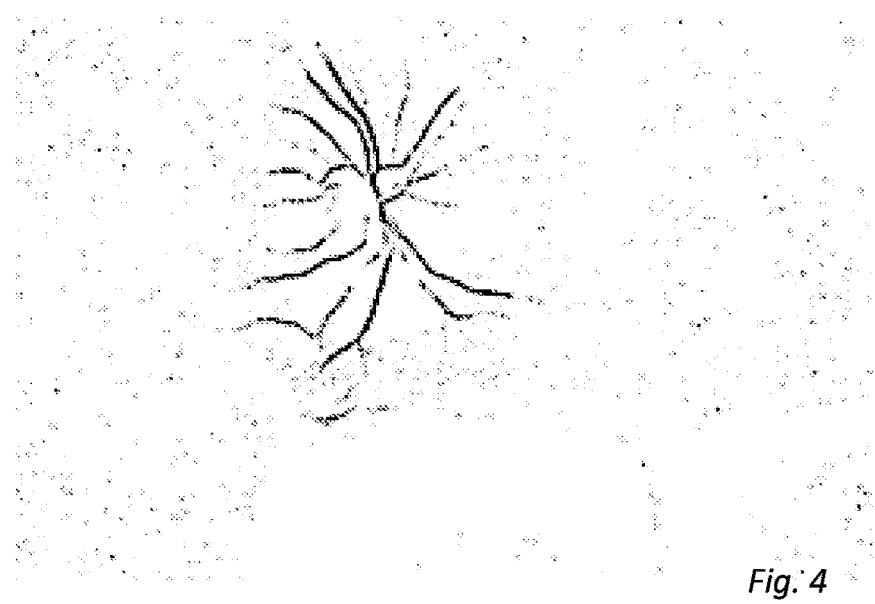
FIG. 4 is a binary image prepared from the full frame image of FIG. 2 by performing adaptive thresholding.

After applying an adaptive thresholding technique, the next sub-step in determining the ROI of the image is to perform a coarse grid search where a sub-sample of pixels within a circular area of a predetermined size are inspected to determine where the area of highest vascular density exists within the source image (as illustrated in FIG. 4, the vascular regions of the binary image are shown with black pixels). The sub-sample of pixels within a circular area of a predetermined size may be inspected by inspecting an array of point offsets that reference a random sub-sample of point offsets within a circular region. For performance reasons size parameter should be selected during software initialization rather than every time a new frame is being inspected.

Determination of the area of highest vascular density may be made utilizing the following or similar code. The function (Set numSamplePoints) can in certain embodiments be set to around 10% of the total pixel count within the circular actual retinal image area that will comprise the ROI. A lower percentage can be used to improve computational performance.

```
numSamplePoints=imageWidth*imageHeight*0.10;
pointCnt=0;
```

```
while(pointCnt<numSamplePoints) {
    double randomX = (double)((rand.nextInt((int)(testRadius)*2))-
        testRadius);
    double randomY = (double)((rand.nextInt((int)(testRadius)*2))-
        testRadius);
    double randomRadius =
        Math.sqrt((randomX*randomX)+(randomY*randomY));
    if(randomRadius<=testRadius) {
        samplePointOffsets[pointCnt]=(randomY*imageWidth)+randomX;
        pointCnt++;
    }
}
```

After constructing an array of point offsets that are to be inspected the entire image may be searched to find the location of the circular area with the highest pixel density, corresponding to the area of highest vascular density and the portion of imaging chip containing the retinal image using the following or similar code.

```
bestHitCnt=0;
xStep=10; // Finer stepping will be more accurate but slower
yStep=10;
minX=(int)testRadius+1;
minY=(int)testRadius+1;
maxX=imageWidth-(int)testRadius;
maxY=imageHeight-(int)testRadius;
for(int x=minX;x<maxX;x+=xStep) {
    hitCnt=0;
    for(int y=minY;y<maxY;y+=yStep) {
// Sum up the point vascular hits for each size circle location
        for(int z=0;z<numSamplePoints;z++) {
            if (adaptiveImageBuff[((y * imageWidth) + x) +
                samplePointOffsets[z]] == 0x00) {
                hitCnt++;
            }
        }
    }
    if(hitCnt>bestHitCnt) {
        bestCenterXLocation=x;
        bestCenterYLocation=Y
    }
}
```

Figure 5:
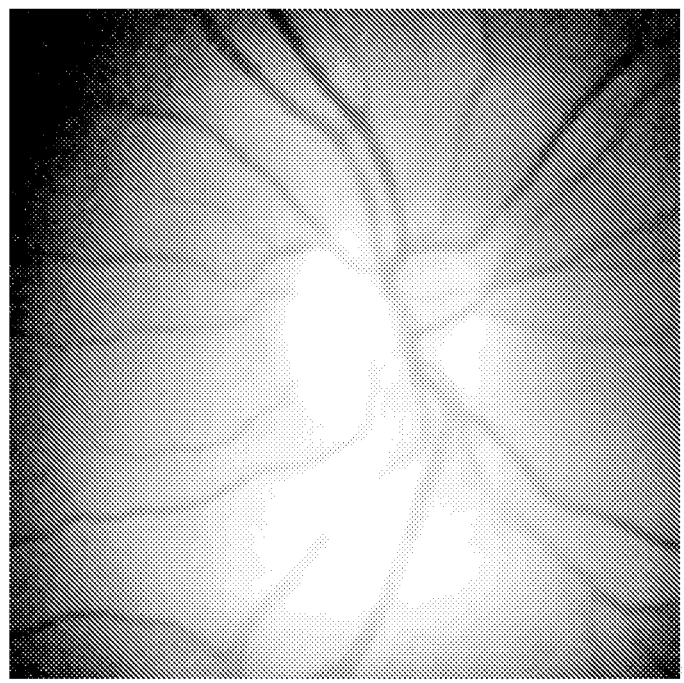
FIG. 5 is a cropped image prepared from the full frame image of FIG. 2.
Figure 6:
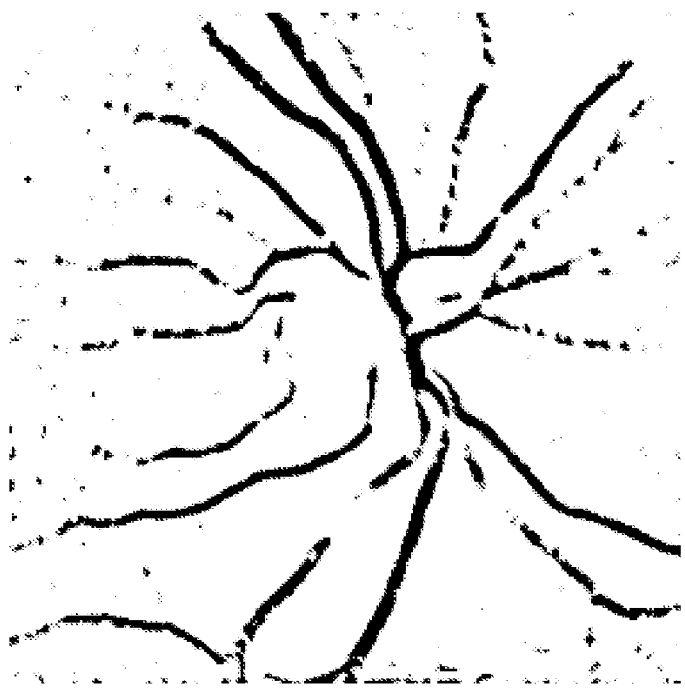
FIG. 6 is a cropped binary image prepared from the full frame image of FIG. 2 by performing adaptive thresholding and cropping based upon a determined ROI.
Figure 7:
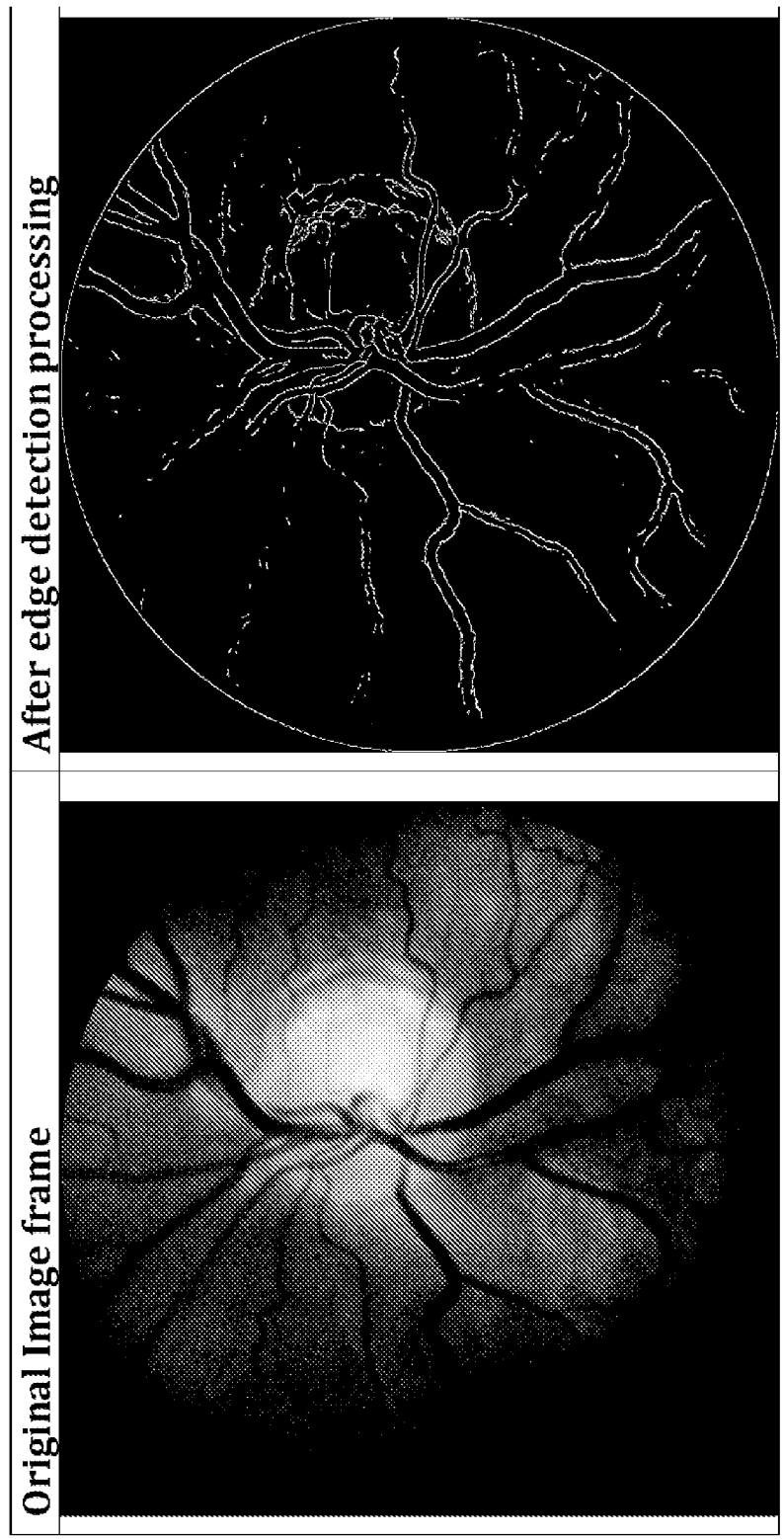
FIG. 7 is an image comparison of an original image frame and the frame after edge detection processing to create a binary image.

Upon completion of the foregoing or similar routines, BestCenterXLocation and BestCenterYLocation show the location of a circular area that contains the highest density of vasculature, and bestHitCnt contains the number of sampled pixels that were marked as black in the adaptive threshold step. When bestHitCnt (or a similar parameter) exceeds a pre-determined value for the level of vasculature within the image processing may continue. In particular, the foregoing or similar routines are applied to determine the ROI of each individual image and the image may be cropped to preserve the ROI and delete extraneous data. For example FIG. 5 is the full frame image of FIG. 3 cropped to include only the ROI determined as described above. FIG. 6 is a corresponding binary image after application of adaptive thresholding and cropping.

As each downsized image is prepared and cropped to the ROI, the system and method will measure image attributes within the ROI such as focus quality, average red, green and blue values, and standard deviations of each individual color layer, uniformity of illumination, and corneal glare to verify that all measured image attributes fall within acceptable ranges (Step 112). Averages and standard deviations are both calculated using traditional methods, and the focus calculation can be implemented via inspection and summing of each individual pixel value to determine the absolute value of the difference between it and nearest neighboring pixels. While this simplistic focus analysis method performs very well for the described purposes, more complex methods such as focus analysis via FFT could also be implemented for focus measurement. For performance reasons a subset of the pixels in the downsized image are inspected for image attribute calculation. This subset inspection is implemented by utilizing step sizes of more than one pixel vertically and horizontally during image frame analysis. Typically, statistically meaningful gathering of these image attributes can be obtained by inspecting 10-20% of the image pixels. If any of the measured attributes do not fall within a pre-define range of acceptability, the image frame is discarded and no further processing steps are performed on the current frame. This analysis of image attributes works very well for discarding spurious images such as pictures of the exam room or the patient's face, which would be out of focus because retinal imaging is done at close to an infinite focus.

Next, the system and method will perform real-time edge detection on each individual video frame to create a binary representation of the vasculature of each retinal image (Step 114). There are several edge detection algorithms that are very well suited for this step such as Sobel, Roberts, Prewitt, and Canny edge detection algorithms. The Canny edge detection algorithm is particularly well suited for the performing edge detection on retinal images because of its inherent ability to suppress noise, and to detect a wide range of edges due to contrast differences from one portion of an image to another. The Canny edge detection algorithm can be parameterized using several different settings to control threshold upper and lower ranges, as well as blur sizes for pre-processing before performing the actual edge detection. These parameters must be optimized to yield binary images maximizing detected retinal vasculature while minimizing the detection of spurious edges created by other digital noise in the source image frame.

Although all of the suitable edge detection techniques can be run on a traditional smartphone CPU 116, these processes are particularly well suited for being implemented on a modern GPU (Graphics Processing Unit) 114 that exists on all modern smartphones because of the GPU's ability to perform vector processing on a massively parallel scale. Depending upon the hardware used for deployment, GPU based edge detection is typically twenty to sixty times faster than performing similar algorithms strictly on a traditional CPU typically found on the industry leading smartphones.

A comparison of an original cropped image frame to the binary output generated through a well parameterized edge detection algorithm after the foregoing processing steps will be similar to the images of FIG. 3.

Because a relatively high frame-rate (at least ten frames per second) is desirable during a typical retinal exam for screening purposes, there is a need to create summary information that can be used to rapidly analyze each video frame to determine what portion of the retinal image the frame contains relative to previously captured image frames without performing a computationally intensive image fit analysis of the frame at various alignments. The disclosed system and method utilize vascular branches and bends by identifying them as points of interest (POI's) that will be common from one image frame to another given two image frames that have an area of overlap showing common image features (Step 116). There are several "Corner Detection" and "Feature Detection" algorithms that are well suited for use with the disclosed methods and systems, but the Shi-Tomasi corner detection algorithm performs particularly well.

The Shi-Tomasi corner detection algorithm is applied to the output image from the edge detection performed in step 114. Performing feature detection on a binary image yields much more reliable feature detection than can typically be performed by running feature detection algorithms on the raw images from the original source video frame. While the techniques described herein can handle both missed features of interest, and spurious detection of features of interest, it is important to tune the feature extraction (Shi-Tomasi) algorithm's blur size, sensitivity, and threshold to maximize the detection of detected features that will be common from one frame to the next when capturing image frames containing overlap, while minimizing the detection of spurious detected features created by other noise in the digital image. For the same reasons specified in step 114, step 116 is also particularly well suited for GPU 114 based algorithm implementation. The detected corners from this processing step are stored in an array of xPts[ ] and yPts[ ] so that they can be utilized by subsequent processing steps.

Figure 8:
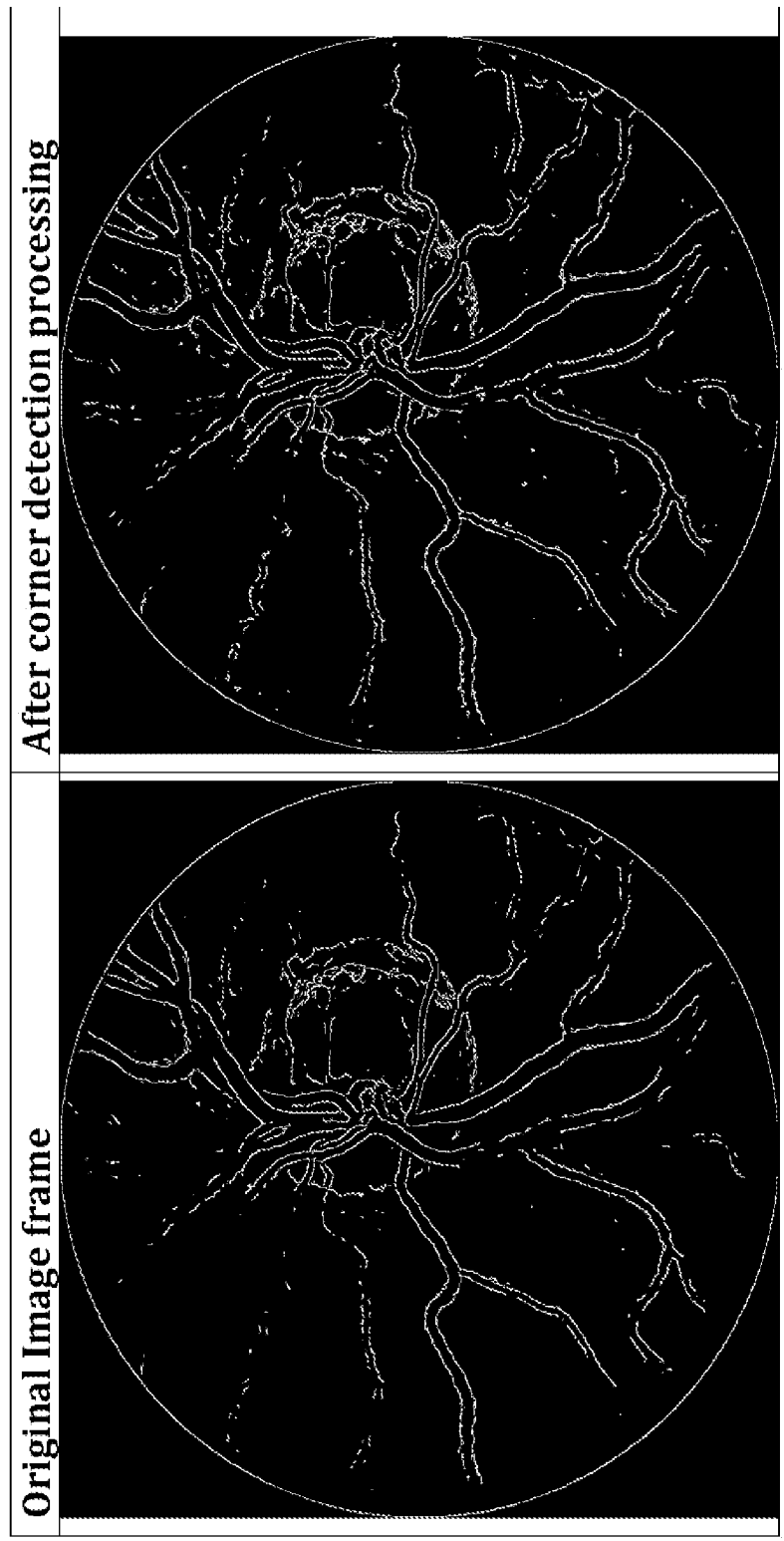
FIG. 8 is an image comparison of the binary image of FIG. 3 before and after point of interest detection.

The image of FIG. 8 shows detected features from a typical retinal image after performing Shi-Tomasi corner detection on the binary image, in step 116.

The results of processing steps 112-116 yield a binary image showing retinal vasculature and arrays of (X, Y) coordinates representing selected features of interest. The next step in image processing is to populate a data structure which contains summary information of each incoming image frame, as well as the original RGB image bytes for the non-downsized frame (Step 118). The data structure may be of any suitable type which contains relative POI position information. Generation and population of the data structure may be accomplished with any suitable software or code. Representative code suitable to accomplish the foregoing step is included below. It is important to note that the following code (and all instances of code contained in this disclosure) is highly simplified and constitutes only representative, nonexclusive, code samples. The disclosed methods may be implemented with any suitable code or data structure.

```
struct frame {
    Byte *    imgBytes;             // RGB image bytes
    double    frameFocusScore;      // Focus measurement
    short     detectedPointCnt;     // Detected Points
    short     xPts[ ];              // X Coordinates
    short     yPts[ ];              // Y Coordinates
    short     pointRelativity[ ][ ][ ]; // Explained Below
    short     relativeXLocation;    // X Offset in panorama
    short     relativeYLocation;    // Y Offset in Panorama
};
```

The three dimensional array "pointRelativity" requires more detailed explanation, as this array is the main element of summary frame information that allows for rapid comparison with other image frames to look for possible image feature overlap as is described below. This array is uniquely designed to allow for extremely rapid comparison (with allowed error), without the need for any computationally intensive operation when the array is compared to the array calculated for other image frames.

Initially, the pointRelativity array may be zeroed to prepare it for processing on a current image frame. To accomplish zeroing, the system and method can use the following sample, representative code or code providing similar functionality:

```
for (int x=0;x<detectedPointCount;x++) {
    for (int y=0;y<POIDisIdxs;y++) {
        for(int z=0;z<POIRotationalSlots;z++) {
            keptFrames[idx].pointRelativity[x][y][z]=0;
        }
    }
}
```

For some or every detected point within the source frame, the system and method may then compute the relative distance and angle from that point to every other detected point in the image frame. Because detected points can be detected with some level of variance and error from one image frame to another, the method preferably rounds both the distance between each point, and the angle from one point to the next by a pre-defined number of pixels and degrees, and populates the pointRelativity array with the results (Step 118).

Step 118 can be performed using the following representative code or similar routines:

```
int ptCnt=keptFrames[idx].detectedPointCnt;
for(int x=0;x<ptCnt;x++) { // For every point in the image
    x1=keptFrames[idx].xPts[x]-(imageWidth/2); // 4 Coord pt
    y1=keptFrames[idx].yPts[x]-(imageHeight/2);// 4 Coord Pt
    // Don't count corners detected because of the iris
    if(sqrt((x1*x1)+(y1*y1))<=((imageWidth/2.0)*0.97)) {
        for(int y=0; y<ptCnt;y++) { // Compare to all points
            xDif=keptFrames[idx].xPts[x]-
                 keptFrames[idx].xPts[y];
                 yDif=keptFrames[idx].yPts[x]-
                 keptFrames[idx].yPts[y];
            double dist=sqrt((xDif*xDif)+(yDif*yDif));
            int ptIdx=
                    ((dist+(POIDistanceRoundingForAlignment/
                    2.0))/
                    POIDistanceRoundingForAlignment); // Round the
                    distance
            double rotationalRadians=
                    atan((double)yDiff/(double)xDiff);
                    double rotationalDegrees =
                    atan2(yDiff, xDiff) * 180.0 / M_PI;
            if (rotationalDegrees < 0.0) {
                rotationalDegrees+=360.0;
            }
            // Round the relative angle
            int rotationalSlot=
((rotationalDegrees+(POIRotationalDegreesRoundingForAlignment/2.0))/
POIRotationalDegreesRoundingForAlignment);
            keptFrames[idx].pointRelativity[x][ptIdx][rotationalSlot]++;
        }
    }
}
```

The following example may be considered to illustrate how the pointRelativity array is populated, and how this information can be utilized. If the method rounds the pixel distance to the nearest 5 pixels, and the relative angle from one point to the next is rounded to the nearest 10 degrees, then:

if pointRelativity[4][50][2]=5, indicates that there are 5 pixels at a rounded distance of 250 pixels (50*5 pixels for distance rounding), at a rounded angle of twenty degrees (2*10 degrees for rounding).

After the foregoing processing steps, the point summary information is now stored in a format allowing for extremely fast comparison (with rounding error) from one image frame to the next, showing how all detected points are related to all other detected points in the image frame in terms of both the distance between points, and the relative angle from one point to the next. The fact that the method performs rounding on the angle measurements allows the selected algorithm to function properly even when minor changes are made to the angle of the camera relative to the patient's eye, without having to perform computationally intensive triangle geometry showing more complex angular relationships between points.

Example 1

To illustrate how the pointRelativity array can be used to rapidly find areas of commonality between two images of the same retina taken at different positions FIG. 9 shows two retinal images that contain an area of overlap with common points of interest within the overlap region. To keep things fairly simple, only four points of interest have been marked in each of the two sample image frames illustrated in FIG. 5. In practice, there would likely be many more marked points in each frame.

Frame #1 Point to point distances (in pixels):

|  | PT#1 | PT#2 | PT#3 | PT#4 |
| --- | --- | --- | --- | --- |
| PT#1 | 0.0 | 68.5 | 64.5 | 51.0 |
| PT#2 | 68.5 | 0.0 | 25.3 | 36.1 |
| PT#3 | 64.5 | 25.3 | 0.0 | 16.4 |
| PT#4 | 51.0 | 36.1 | 16.4 | 0.0 |

Frame #2 Point to point distances (in pixels):

|  | PT#1 | PT#2 | PT#3 | PT#4 |
| --- | --- | --- | --- | --- |
| PT#1 | 0.0 | 64.8 | 61.4 | 46.1 |
| PT#2 | 64.8 | 0.0 | 22.2 | 34.2 |
| PT#3 | 61.4 | 22.2 | 0.0 | 18.0 |
| PT#4 | 46.1 | 34.2 | 18.0 | 0.0 |

Frame #1 Point to point distances (rounded to the nearest 22 pixels):

|  | PT#1 | PT#2 | PT#3 | PT#4 |
| --- | --- | --- | --- | --- |
| PT#1 | 0 | 66 | 66 | 44 |
| PT#2 | 66 | 0 | 22 | 44 |
| PT#3 | 66 | 22 | 0 | 22 |
| PT#4 | 44 | 44 | 22 | 0 |

Frame #2 Point to point distances (rounded to the nearest 22 pixels):

|  | PT#1 | PT#2 | PT#3 | PT#4 |
| --- | --- | --- | --- | --- |
| PT#1 | 0 | 66 | 66 | 44 |
| PT#2 | 66 | 0 | 22 | 44 |
| PT#3 | 66 | 22 | 0 | 22 |
| PT#4 | 44 | 44 | 22 | 0 |

Frame #1 Point to point angles (in degrees):

|  | PT#1 | PT#2 | PT#3 | PT#4 |
| --- | --- | --- | --- | --- |
| PT#1 | 0.0 | 61.2 | 82.3 | 92.2 |
| PT#2 | 241.2 | 0.0 | 170.1 | 194.4 |
| PT#3 | 262.9 | 350.9 | 0.0 | 232.4 |
| PT#4 | 272.2 | 14.4 | 52.4 | 0.0 |

Frame #2 Point to point angles (in degrees)

|  | PT#1 | PT#2 | PT#3 | PT#4 |
| --- | --- | --- | --- | --- |
| PT#1 | 0.0 | 63.4 | 83.5 | 93.7 |
| PT#2 | 243.4 | 0.0 | 172.2 | 200.6 |
| PT#3 | 263.5 | 352.2 | 0.0 | 236.3 |
| PT#4 | 273.7 | 20.6 | 56.3 | 0.0 |

Frame #1 Point to point angles (rounded to the nearest 10 degrees):

|  | PT#1 | PT#2 | PT#3 | PT#4 |
| --- | --- | --- | --- | --- |
| PT#1 | 0 | 60 | 80 | 90 |
| PT#2 | 240 | 0 | 170 | 190 |
| PT#3 | 260 | 350 | 0 | 230 |
| PT#4 | 270 | 10 | 50 | 0 |

Frame #2 Point to point angles (rounded to the nearest 10 degrees):

|  | PT#1 | PT#2 | PT#3 | PT#4 |
| --- | --- | --- | --- | --- |
| PT#1 | 0 | 60 | 80 | 90 |
| PT#2 | 240 | 0 | 170 | 200 |
| PT#3 | 260 | 350 | 0 | 240 |
| PT#4 | 270 | 20 | 60 | 0 |

Because the method is using rounded distances and rounded angles as attributes representing the relationships of points, the method can divide the rounded distance by the distance rounding factor, and divide the rounded rotational degrees by the rotation rounding factor in order to reduce memory requirements for the pointRelativity array. One benefit of using rounded distances and rounded angles is to greatly reduce the likelihood of a distance or an angle falling near to a rounded angle or distance in one frame, and having it fall on the other side for rounding purposes in a subsequent frame.

As tabulated above, for frame #1, the rounded distance between point 1 and point 2 is 66 pixels (rounded to the nearest 22 pixels). The method may take this distance, and divides it by the distance rounding factor of 22 pixels to get a distance index value of 3 for the distance from point 1 and point 2 in frame #1.

For frame #1, the rounded angle between point 1 and point 2 is 60 degrees (rounded to the nearest 10 degrees). The method may take this distance, and divide it by the angle rounding factor of 10 degrees to get an angle index value of 6 for the angle between point 1 and point 2 in frame #1. So, the relationship between point 1 and point 2 in frame 1 can be represented in the pointRelativity array as follows:

pointRelativity[1][3][6]=pointRelativity[1][3][6]+1;

The foregoing indicates that frame 1 has a point of interest in it that is 66 pixels away from another point (66/22=3), at a relative angle of 60 degrees (60/10).

Once all points in each frame have been processed in this manner, it is extremely fast and efficient to determine if two frames are likely to contain the same features.

After performing edge detection, feature extraction, and computing point summary information for the image frame, the method will next compare the image frame to all other currently stored image frames in order to determine if the current image frame represents a newly imaged area of the retina, or if other images have already been captured of the same relative area of the retina (Step 120). If the image frame represents a newly imaged area of the retina, or if it is determined to be of better quality than an existing frame, it is added to the image panorama (Step 122).

Because of the clean structure, and pre-rounding done to point summary information, the comparison of this subject frame to all currently kept image frames may be performed very rapidly with fairly simplistic code, for example the code summarized below which compares the current frame to another previously captured frame that still resides in memory. This type of or a similar comparison must be done to compare the image to all previously retained images:

```
for(int x=0;x<frame1.detectedPointCnt;x++) {
    for(int y=0;y<frame2.detectedPointCnt;y++) {
        int totalInCommon=0;
        for(int z=0;z<MaxDistanceSlots;z++) {
            for(int rot=0;rot<360/MaxRotationSlots;rot++) {
                totalInCommon+=
                    abs(frame1.pointRelativity[x][z][r]-
                frame2.pointRelativity[y][z][r]);
                -    Maintain a list of the highest scoring
                -    LikelyFrame1PTs[ ] and
                     LikelyFrame2Pts[ ]
                -    Based upon the highest
                     totalInCommon
                -    Scores.
        }
    }
}
```

While the above algorithm works well for finding possible alignment points between two image frames, more complex analysis of the pointRelativity data structure may be desired using techniques to enhance the likelihood of finding alignment points that may be missed via the foregoing or similar relatively simple analysis of the pointRelativity data structure.

After executing the above or similar code, the method can examine the (x, y) coordinates represented by likelyFrame1PT[ ], and likelyFrame2PT[ ] to determine a possible offset that can be utilized to join the two frames together to yield a larger image showing a greater field of view than the two individual image frames.

For example, if LikelyFrame1PT[1]=(200,100) and LikelyFrame2PT[1]=(200, 300) the method determines that a possible image fit exists if image #2 is shifted up vertically be 200 pixels (300-100). The method may iterate through all possible alignments found by the code listed above (or code providing similar functionality) and calculate the best possible fit which is the one that has the highest computed image correlation statistic. If the best image correlation score exceeds a pre-defined value, all pixels in the source frame are added to the panorama, unless a previous frame of a higher image quality as determined in step 112 containing the same image pixels has already been added to the panorama.

The final image processing step includes measurement of the field of view of the image panorama by expanding outwards in a circular fashion from the center point (Step 124). If the captured field of view exceeds an operator defined or hardcoded value, the camera or smartphone is controlled by the process to automatically complete the already computed image panorama is presented. If the targeted field of view has not yet been achieved, the method will control the camera or smartphone to continue processing incoming frames in the above fashion.

Figure 10:
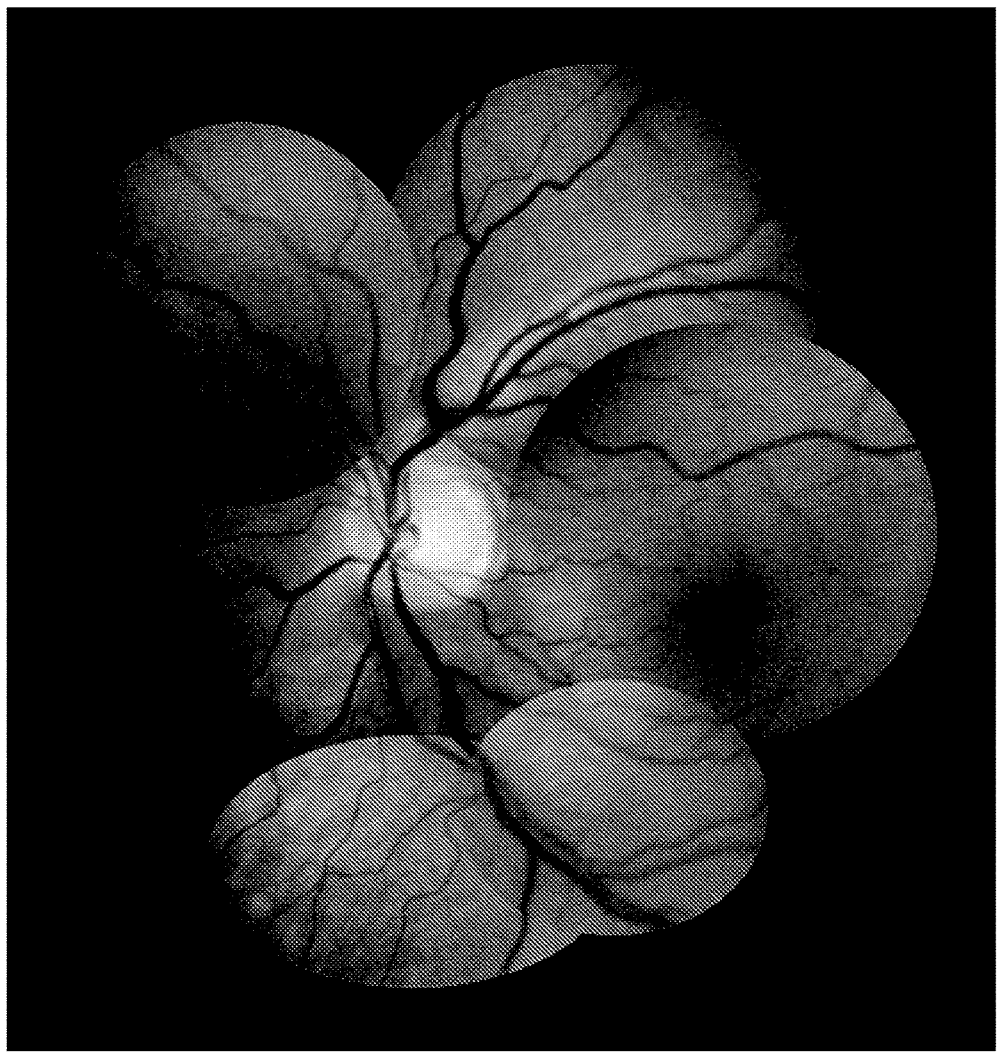
FIG. 10 is a representative wide field retinal mosaic created according to the methods disclosed herein

By automatically determining the ROI, cropping, pre-qualifying all incoming video frames based on selected image parameters, and determining possible alignment (or commonality) with all previously retained images frames, the method is able to acquire a set of image frames that meet pre-defined requirements for quality and calculate the relative offsets between each frame to have the software autonomously terminate image capture and present the user with a relatively wide-angle retinal panorama such as shown in FIG. 10.

As noted above, one apparatus embodiment 200 includes a smartphone 202 having a GPU 214, CPU 216, memory 212 and other architecture providing for the implementation of the described methods. Alternative embodiments may include a dedicated ophthalmologic camera or imaging device communicating with a computer of any type which may include software configured to implement the foregoing methods.

Figure 11:
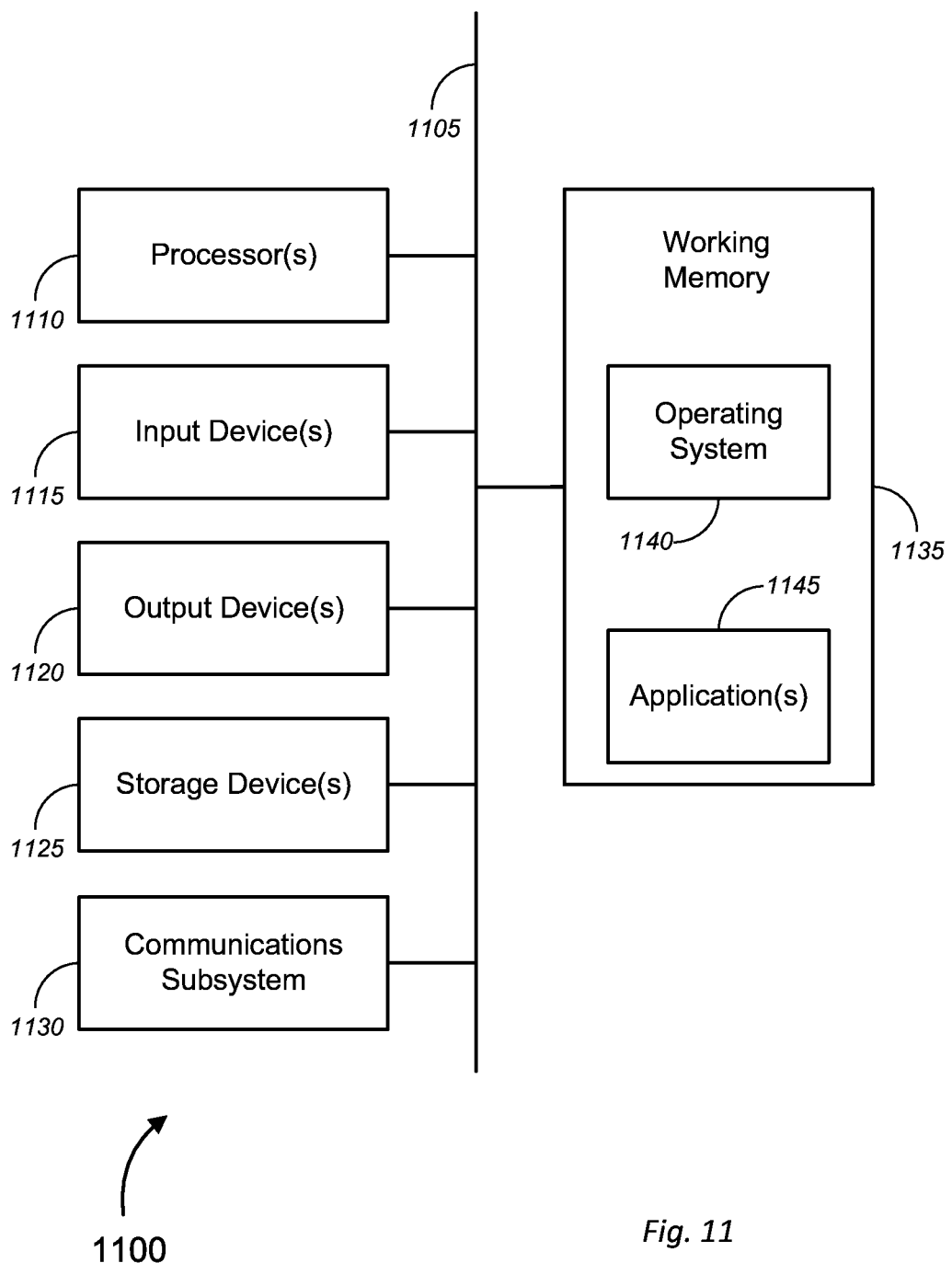
FIG. 11 is a block diagram illustrating an exemplary computer architecture, in accordance with selected embodiments

FIG. 11, is a block diagram illustrating an exemplary computer architecture. FIG. 11 provides a schematic illustration of one embodiment of a computer system 1100 that can perform the methods provided by various other embodiments, as described herein. It should be noted that FIG. 11 is meant only to provide a generalized illustration of various components, of which one or more, or none, of each may be utilized as appropriate. FIG. 11, therefore, broadly illustrates how individual system elements may be implemented in a relatively separated or relatively more integrated manner.

The computer system 1100 is shown comprising hardware elements that can be electrically coupled via a bus 1105, or may otherwise be in communication, as appropriate. The hardware elements may include one or more processors 1110, including without limitation one or more general-purpose processors, or one or more special-purpose processors such as digital signal processing chips, graphics acceleration processors, or the like; one or more input devices 1115, which can include without limitation a mouse, a keyboard, or the like; and one or more output devices 1120, which can include without limitation a display device, a printer, or the like.

The computer system 1100 may further include, or be in communication with, one or more storage devices 1125. The one or more storage devices 1125 can comprise, without limitation, local and/or network accessible storage, or can include, without limitation, a disk drive, a drive array, an optical storage device, a solid-state storage device. The solid-state storage device can include, but is not limited to, one or more of a random access memory ("RAM") or a read-only memory ("ROM"), which can be programmable, flash-updateable, or the like. Such storage devices may be configured to implement any appropriate data stores, including without limitation various file systems, database structures, or the like.

The computer system 1100 might also include a communications subsystem 1130, which can include without limitation a modem, a network card (wireless or wired), an infra-red communication device, a wireless communication device or chipset, or the like. The wireless communication device might include, but is not limited to, a Bluetooth™ device, an 802.11 device, a WiFi device, a WiMax device, a WWAN device, cellular communication facilities, or the like.

The communications subsystem 1130 may permit data to be exchanged with a network, with other computer systems, with any other devices described herein, or with any combination of network, systems, and devices. According to some embodiments, a network might include a local area network ("LAN"), including without limitation a fiber network, an Ethernet network, a Token-Ring™ network, and the like; a wide-area network ("WAN"); a wireless wide area network ("WWAN"); a virtual network, such as a virtual private network ("VPN"); the Internet; an intranet; an extranet; a public switched telephone network ("PSTN"); an infra-red network; a wireless network, including without limitation a network operating under any of the IEEE 802.11 suite of protocols, the Bluetooth™ protocol, or any other wireless protocol; or any combination of these or other networks. In many embodiments, the computer system 1100 will further comprise a working memory 1135, which can include a RAM or ROM device, as described above.

The computer system 1100 may also comprise software elements, shown as being currently located within the working memory 1135, including an operating system 1140, device drivers, executable libraries, or other code. The software elements may include one or more application programs 1145, which may comprise computer programs provided by various embodiments, or may be designed to implement methods and/or configure systems provided by other embodiments, as described herein. Merely by way of example, one or more procedures described with respect to the methods discussed above might be implemented as code or instructions executable by a computer or by a processor within a computer. In an aspect, such code or instructions can be used to configure or adapt a general purpose computer, or other device, to perform one or more operations in accordance with the described methods.

A set of these instructions or code might be encoded and/or stored on a non-transitory computer readable storage medium, such as the storage devices 1125 described above. In some cases, the storage medium might be incorporated within a computer system, such as the system 1100. In other embodiments, the storage medium might be separate from a computer system—that is, a removable medium, such as a compact disc, or the like. In some embodiments, the storage medium might be provided in an installation package, such that the storage medium can be used to program, configure, and/or adapt a general purpose computer with the instructions/code stored thereon. These instructions might take the form of executable code, which is executable by the computer system 1100, or might take the form of source or installable code. The source or installable code, upon compilation, installation, or both compilation and installation, on the computer system 1100 might take the form of executable code. Compilation or installation might be performed using any of a variety of generally available compilers, installation programs, compression/decompression utilities, or the like.

It will be apparent to those skilled in the art that substantial variations may be made in accordance with specific requirements. For example, customized hardware—such as programmable logic controllers, field-programmable gate arrays, application-specific integrated circuits, or the like—might also be used. In some cases, particular elements might be implemented in hardware, software (including portable software, such as applets, etc.), or both. Further, connection to other computing devices such as network input/output devices may be employed.

As mentioned above, in one aspect, some embodiments may employ a computer system, such as the computer system 1100, to perform methods in accordance with various embodiments of the invention. According to a set of embodiments, some or all of the procedures of such methods might be performed by the computer system 1100 in response to processor 1110 executing one or more sequences of one or more instructions. The one or more instructions might be incorporated into the operating system 1140 or other code that may be contained in the working memory 1135, such as an application program 1145. Such instructions may be read into the working memory 1135 from another computer readable medium, such as one or more of the storage devices 1125. Merely by way of example, execution of the sequences of instructions contained in the working memory 1135 might cause the one or more processors 1110 to perform one or more procedures of the methods described herein.

The terms "machine readable medium" and "computer readable medium," as used herein, refer to any medium that participates in providing data that causes a machine to operate in a specific fashion. In an embodiment implemented using the computer system 1100, various computer readable media might be involved in providing instructions or code to the one or more processors 1110 for execution, might be used to store and/or carry such instructions/code such as signals, or both. In many implementations, a computer readable medium is a non-transitory, physical, or tangible storage medium. Such a medium may take many forms, including, but not limited to, non-volatile media, volatile media, and transmission media. Non-volatile media includes, for example, optical disks, magnetic disks, or both, such as the storage devices 1125. Volatile media includes, without limitation, dynamic memory, such as the working memory 1135. Transmission media includes, without limitation, coaxial cables, copper wire and fiber optics, including the wires that comprise the bus 1105, as well as the various components of the communication subsystem 1130, or the media by which the communications subsystem 1130 provides communication with other devices. Hence, transmission media can also take the form of waves, including without limitation radio, acoustic, or light waves, such as those generated during radio-wave and infra-red data communications.

Common forms of physical or tangible computer readable media include, for example, a floppy disk, a flexible disk, a hard disk, magnetic tape, or any other magnetic medium; a CD-ROM, DVD-ROM, or any other optical medium; punch cards, paper tape, or any other physical medium with patterns of holes; a RAM, a PROM, an EPROM, a FLASH-EPROM, or any other memory chip or cartridge; a carrier wave; or any other medium from which a computer can read instructions or code.

While certain features and aspects have been described with respect to exemplary embodiments, one skilled in the art will recognize that numerous modifications are possible. For example, the methods and processes described herein may be implemented using hardware components, software components, and/or any combination thereof. Further, while various methods and processes described herein may be described with respect to particular structural and/or functional components for ease of description, methods provided by various embodiments are not limited to any particular structural and/or functional architecture but instead can be implemented on any suitable hardware, firmware and/or software configuration. Similarly, while certain functionality is ascribed to certain system components, unless the context dictates otherwise, this functionality can be distributed among various other system components in accordance with the several embodiments.

Moreover, while the procedures of the methods and processes described herein are described in a particular order for ease of description, unless the context dictates otherwise, various procedures may be reordered, added, and/or omitted in accordance with various embodiments. Moreover, the procedures described with respect to one method or process may be incorporated within other described methods or processes; likewise, system components described according to a particular structural architecture and/or with respect to one system may be organized in alternative structural architectures and/or incorporated within other described systems. Hence, while various embodiments are described with—or without—certain features for ease of description and to illustrate exemplary aspects of those embodiments, the various components and/or features described herein with respect to a particular embodiment can be substituted, added and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A method of generating a wide field retinal image comprising:
   controlling a camera to capture a video stream of individual retinal images;
   storing the individual retinal images in a memory associated with the camera;
   downsizing a plurality of the individual retinal images to create a plurality of downsized images;
   performing edge detection on a plurality of the downsized images to yield a plurality of binary images;
   identifying points of interest corresponding to vascular structures in a plurality of the binary images;
   determining a coordinate position array of the identified points of interest in the binary images;
   populating a data structure with the coordinate position arrays of multiple binary images;
   comparing the coordinate position arrays of multiple binary images to determine an overlapping image alignment among the multiple binary images; and
   combining the individual retinal images corresponding to the multiple binary images into a panorama in accordance with the determined overlapping image alignment.

2. The method of claim 1 further comprising:
   determining a location on a sensor of the camera where an individual image is located;
   determining a region of interest in the individual image; and
   cropping the individual image to preserve the region of interest.

3. The method of claim 2 further comprising:
   measuring one or more image attributes of the downsized images; and
   discarding unsuitable images based upon the measured image attributes of the downsized images.

4. The method of claim 3 further comprising:
   determining whether a downsized retinal image is of a higher quality than another downsized retinal image showing an overlapping retinal structure; and
   discarding the lower quality image.

5. The method of claim 1 further comprising:
   measuring the field of view of the combined full resolution retinal image; and
   terminating the process upon achievement of a designated field of view.

6. The method of claim 5 wherein all steps are completed during an ocular examination.

7. A retinal imaging system comprising:
   a smartphone comprising a camera lens, and illumination source, and imaging chip and imaging electronics;
   a supplemental optic configured to mate with the smartphone lens and provide for the focusing of an image of a retina on the smartphone imaging chip;
   and one or more processors within the smartphone;
   one or more non-transitory computer readable media located within the smartphone having stored thereon software comprising a set of instructions that, when executed by the one or more processors, causes the system to perform one or more functions, the set of instructions comprising:
      instructions to control the smartphone to capture a video stream of individual retinal images with the smartphone camera lens, illumination source, imaging chip and imaging electronics;
      instructions to store the individual retinal image in a memory;
      instructions to downsize a plurality of the individual retinal images to create downsized images;
      instructions to perform edge detection on a plurality of the downsized images to yield a plurality of binary images;
      instructions to identify points of interest corresponding to vascular structures in a plurality of the binary images;
      instructions to determine a coordinate position array of the identified points of interest in the binary images;
      instructions to populate a data structure with the coordinate position arrays of multiple binary images;
      instructions to compare the coordinate position arrays of multiple binary images to determine an overlapping image alignment among the multiple binary images;
      instructions to combine the individual retinal images corresponding to the multiple binary images into a panorama in accordance with the determined overlapping image alignment.

8. The system of claim 7 wherein the set of instructions further comprise:
   instructions to determine a location on the imaging chip of the smartphone where an individual image is located;
   instructions to determine a region of interest in the individual image; and
   instructions to crop the individual image to preserve the region of interest.

9. The system of claim 8 wherein the set of instructions further comprise:
   instructions to measure one or more image attributes of the downsized images; and
   instructions to discard unsuitable images based upon the measured image attributes of the downsized images.

10. The system of claim 9 wherein the set of instructions further comprise:
    instructions to determine whether a downsized retinal image is of a higher quality than another downsized retinal image showing an overlapping retinal structure; and
    instructions to discard the lower quality image.

11. The system of claim 7 wherein the set of instructions further comprise:
   instructions to measure the field of view of the combined full resolution retinal image; and
   instructions to terminate the process upon achievement of a designated field of view.

12. The system of claim 11 wherein the set of instructions further cause all instructions to be completed during an ocular examination.

13. A retinal imaging system comprising:
   an ophthalmoscope;
   a digital imaging device incorporated within, or attached to the ophthalmoscope;
   and one or more processors in digital communication with the digital imaging device;
   one or more non-transitory computer readable media in digital communication with the one or more processors having stored thereon software comprising a set of instructions that, when executed by the one or more processors, causes the system to perform one or more functions, the set of instructions comprising:
      instructions to capture a video stream of individual retinal images;
      instructions to store the individual retinal images in a memory;
      instructions to downsize a plurality of the individual retinal images to create downsize images;
      instructions to perform edge detection on a plurality of the downsized images to yield a plurality of binary images;
      instructions to identify points of interest corresponding to vascular structures in a plurality of the binary images;
      instructions to determine a coordinate position array of the identified points of interest in the binary images;
      instructions to populate a data structure with the coordinate position arrays of multiple binary images;
      instructions to compare the coordinate position arrays of multiple binary images to determine an overlapping image alignment among the multiple binary images;
      instructions to combine the individual retinal images corresponding to the multiple binary images into a panorama in accordance with the determined overlapping image alignment.

14. The system of claim 13 wherein the set of instructions further comprise:
   instructions to determine a location on the imaging chip of the smartphone where an individual image is located;
   instructions to determine a region of interest in the individual image; and
   instructions to crop the individual image to preserve the region of interest.

15. The system of claim 14 wherein the set of instructions further comprise:
   instructions to measure one or more image attributes of the downsized images; and
   instructions to discard unsuitable images based upon the measured image attributes of the downsized images.

16. The system of claim 15 wherein the set of instructions further comprise:
   instructions to determine whether a downsized retinal image is of a higher quality than another downsized retinal image showing an overlapping retinal structure; and
   instructions to discard the lower quality image.

17. The system of claim 13 wherein the set of instructions further comprise:
   instructions to measure the field of view of the combined full resolution retinal image; and
   instructions to terminate the process upon achievement of a designated field of view.

18. The system of claim 17 wherein the set of instructions further cause all instructions to be completed during an ocular examination.

* * * * *